United States Patent [19]

Chakerian

[11] Patent Number: Plant 5,724

[45] Date of Patent: Apr. 22, 1986

[54] PLUM TREE, "SWEET HEART"

[76] Inventor: Jonathan P. Chakerian, 269 W. Sycamore, Reedley, Calif. 93654

[21] Appl. No.: 674,028

[22] Filed: Nov. 21, 1984

[51] Int. Cl.[4] ..... A01H 5/03
[52] U.S. Cl. ..... Plt./38
[58] Field of Search ..... Plt./38

*Primary Examiner*—Robert E. Bagwill
*Attorney, Agent, or Firm*—Worrel & Worrel

[57] ABSTRACT

A new and distinct variety of plum tree to be known as the "Sweet Heart" which is most closely similar to the well known Casselman Plum Tree from which it is distinguished by pink rather than white blossoms, large leaves, and larger fruit.

1 Drawing Figure

BACKGROUND OF THE NEW VARIETY

The present invention relates to a new and distinct variety of plum tree which has been named Sweet Heart.

The new variety is broadly characterized by bearing fruit which is substantially similar to that produced by the Casselman Plum Tree (unpatented) with which it ripens at approximately the same time but from which it is distinguished by blossoms which are light pink as distinguished from the white Casselman blossoms. The new variety has larger leaves than the Casselman, produces larger fruit which is thick-skinned and can be picked at the same time as the Casselman. The fruit of the subject variety stores and ships excellently, has smaller seeds, and ripens uniformly so that the entire crop can be picked at one time. The new variety has a much longer picking season and can be permitted to remain on the tree much longer than the Casselman.

ORIGIN AND ASEXUAL REPRODUCTION OF THE NEW VARIETY

For many years, the applicant has sought to produce improved varieties of stone fruit by cross-pollinating blossoms of selected trees of desired characteristics. Pursuant to such objective, the applicant endeavored to cross the Casselman Plum Tree (unpatented) with the Wonderful Pomegranate Tree (unpatented). What resulted may have unintentionally resulted in crossing a Casselman Plum Tree with a Casselman Plum Tree.

The applicant performed the cross-pollination on his farm at 269 W. Sycamore, Reedley, County of Fresno, Calif. The cross-pollination was performed by the applicant in 1978. The applicant was seeking trees of smaller stature which would be easier to pick. His efforts to cross the Casselman Plum with the Wonderful Pomegranate produced eight seeds. The applicant succeeded in germinating six of the seeds which he planted on his farm and grew until he could determine the characteristics of the progeny. The subject variety was noted to have improved characteristics, as hereinafter described, and was asexually reproduced by the applicant on the same farm by budding the new variety into several Santa Rosa Plum Trees (unpatented). The budded trees were carefully observed by the applicant and determined to have the same characteristics as the original seedling that had been selected.

SUMMARY OF THE NEW VARIETY

The instant variety of plum tree is characterized by perpetuating the general tree and fruit characteristics of the Casselman variety of plum tree and which bears fruit which ripens at approximately the same time as the fruit of the Casselman Plum Tree but which is distinguished from the Casselman and characterized as to novelty by having larger leaves, larger fruit, smaller seeds, and thicker skin than the Casselman variety.

BRIEF DESCRIPTION OF THE DRAWING

The accompanying drawing is a color photograph of four whole plums of the subject variety, two being polished and two having the bloom remaining thereon, another plum of the present variety sliced on the suture plane together with a twig showing characteristic leaves of the subject variety and a further twig having the leaves removed therefrom to show stem coloration.

DETAILED DESCRIPTION

Referring more particularly to the pomological details of the new and distinct variety of plum tree, the following has been observed under the ecological conditions prevailing in the above designated orchard near Reedley, Fresno County, Calif. All of the color plate designations are by reference to the Munsell Limit Color Cascade, common descriptive color names also being used.

TREE

Size: Can be pruned to small size and vase form without impairing production.
Vigor: Medium.
Fruit production: Heavy producer on outer ends of scaffold branches.
Trunk characteristics: Normal.

BLOSSOMS

Date of bloom: March 10 to 15.
Color: Light Pink

LEAVES

Size:
*Length.*—10.5 cm. average.
*Width.*—4.6 cm. average.
Form: Elliptic, acuminate; abruptly pointed; Base — Cuneate.

Color: Medium green, Plate 21-15.
Texture: Smooth.
Marginal form: Serrulate.
Petiole:
*Length.*—1.8 cm. average.
*Thickness.*—Medium.
Glands: Average number 3, irregular; opposite; small; globose; brown; positioned at base of blade on petiole.
Stipules: Present.

BRANCHES

Color: Reddish-Brown, Plate 29-14.

FRUIT

Size: Generally symmetrical, large; axial diameter — 5.8 cm. average; diameter transverse in suture plane — 5.6 cm. average; diameter at right angles to suture plane — 5.4 cm. average.
Form: Heart shaped.
Suture: Inconspicuous, shallow line extending from base to apex.
Stem cavity: Shallow; rounded circular; depth — 5 mm. breadth — 5 mm.
Base: Almost flat.
Apex: Ranges from pointed to somewhat rounded viewed along the suture.
Pistil point: Usual.
Stem:
*Length.*—Medium, 1.7 cm. average.
Skin: Medium thickness; medium texture; tenacious to flesh; no observed tendency to crack.
Color: Dark Reddish-Purple, ranges from Plate 40-14 to dark reddish-purple.
Bloom: Heavy, Gray.
Down: Wanting.

FLESH

Color: Amber, Plate 29-2 near the base, with asymmetrical, deep red, Plate 40-14 perfusion, with red color having greater density in proximity to the skin.
Amygdalin: Wanting.
Juice: Scant.
Texture: Firm.
Fibers: Few, fine.
Ripening: Even.
Flavor: Sweet, mild.
Aroma: Slight.
Eating Quality: Very good.
Stone: Semi-freestone.
Size: Small; length — 1.8 cm. average; breadth — 1.5 cm average; thickness — 1.1 cm. average.
Form: Generally oval, slightly pointed toward base.
Base: Generally pointed.
Apex: Slightly flattened.
Sides: Generally symmetrical.
Ridges: Moderate, converging toward base.
Color: Plate 29-11.
Tendency to split: Slight.
Use: Fresh market, shipping.
Keeping quality: Excellent.
Shipping quality: Excellent.

Although the new variety of plum tree possesses the described characteristics as a result of growing conditions prevailing in Fresno County, Calif., it is to be understood that variations of the usual magnitude in characteristics incident to growing conditions, fertilization, pruning and pest control are to be expected.

Having thus described and illustrated my new variety of plum tree, what is claimed as new and desired to be secured by Letters Patent is:

1. A new and distinct variety of plum tree substantially as illustrated and described, characterized by similarity in tree and fruit characteristics to the well known Casselman variety of plum tree but distinguished therefrom and characterized as to novelty by having larger leaves and producing larger fruit having smaller seeds, and thicker skins conducive to superior shipping and storage capabilities as compared with the Casselman Plum Tree.

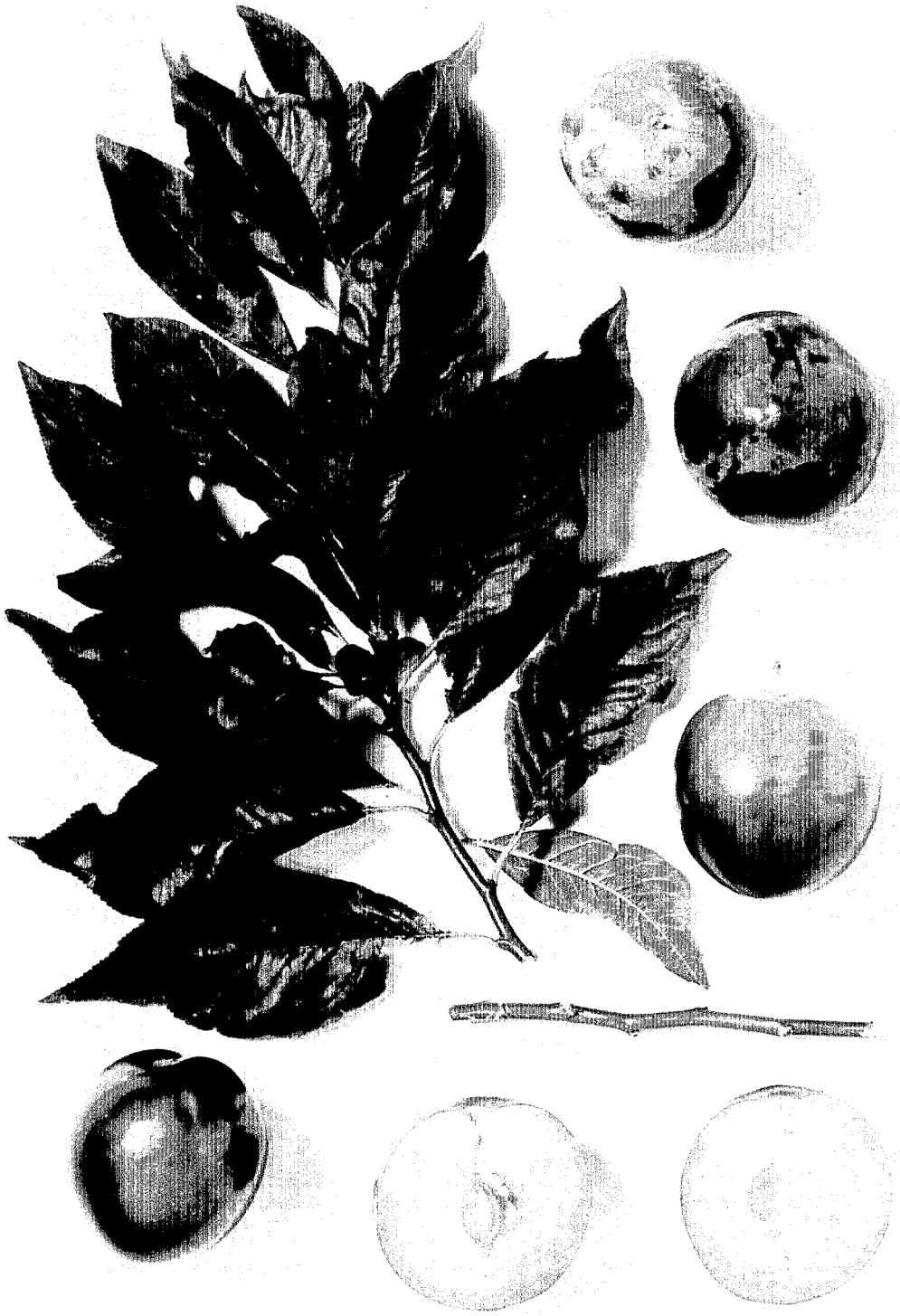

* * * * *